United States Patent [19]

Gleeson, III

[11] Patent Number: 4,892,106

[45] Date of Patent: Jan. 9, 1990

[54] MULTIPLE AFFERENT SENSORY STIMULATION DEVICE

[76] Inventor: William J. Gleeson, III, 2319 W. Rapallo Way, Tucson, Ariz. 85741

[21] Appl. No.: 109,403

[22] Filed: Oct. 19, 1987

[51] Int. Cl.⁴ .................. A61B 13/00; A61N 1/00; H05G 00/00

[52] U.S. Cl. .................. 128/745; 128/421; 128/395; 128/380

[58] Field of Search .............. 128/734, 421, 905, 380, 128/745, 254, 395, 793; 600/26, 27; 360/33.1; 358/343, 330

[56] References Cited

U.S. PATENT DOCUMENTS

| | | | |
|---|---|---|---|
| 3,240,099 | 3/1966 | Irons | 84/464 R |
| 3,292,861 | 12/1966 | Kawamura | 239/17 |
| 3,343,453 | 9/1967 | Butterfield | 353/18 |
| 3,388,699 | 6/1968 | Webb et al. | 600/26 |
| 3,473,428 | 10/1969 | Phillips | 84/464 |
| 3,822,693 | 7/1974 | King | 600/27 |
| 3,919,915 | 11/1975 | Isbell | 84/464 |
| 3,958,113 | 5/1976 | Termohlen | 84/464 |
| 4,097,917 | 6/1978 | McCaslin | 362/234 |
| 4,117,265 | 9/1978 | Gerlach | 179/1 SP |
| 4,172,406 | 10/1979 | Martinez | 84/464 R |
| 4,315,502 | 2/1982 | Gorges | 600/27 |
| 4,542,418 | 9/1985 | Yoneyama et al. | 358/343 |
| 4,564,867 | 1/1986 | Nakajima | 358/343 |
| 4,622,881 | 11/1986 | Rand | 362/235 |
| 4,641,205 | 2/1987 | Beyers, Jr. | 360/33.1 |
| 4,665,926 | 5/1987 | Leuner et al. | 600/26 |
| 4,777,937 | 10/1988 | Rush et al. | 600/27 |

Primary Examiner—Francis Jaworski
Assistant Examiner—George Manuel
Attorney, Agent, or Firm—J. Michael McClanahan

[57] ABSTRACT

A multiple afferent sensory stimulation device is provided to receive a prerecorded tape program upon which the audio stimulation and control signals for the visual stimulation of a subject person's eyes and ears is provided, the invention consisting of a reproducing device to emit the audio and visual control signals on separate left and right channels, the audio stimulation proceeding directly to earphones worn by the subject person, and the visual stimulation control signals processed electronically. The electronic processing includes devices to frequency separate the audio stimulus signals from the control signals, an automatic gain control circuit to assure sufficient amplitude of visual control signals for processing, tone decoders to separate signals energizing the visual stimulus and turning off the visual stimulus, logic circuit to assure certainty of the on and off stimulus control signals, the electrical stimulus provided by an electrical lamp immediately in front of the subject person's eyes. Various different schemes of audio and visual sensory stimulation are suggested for achieving a mental and physical affect upon the subject person.

11 Claims, 2 Drawing Sheets

MULTIPLE AFFERENT SENSORY STIMULATION DEVICE

BACKGROUND OF THE INVENTION

1. Field of the Invention.

The field of the invention is devices which simultaneously provide visual and audio stimulus to a person wearing a set of earphones and goggles with light stimulus in the front of the goggles.

2. Description of Related Art.

Researchers have discovered that through the use of visual and audio stimulus, certain reactions may be induced into a person such as relaxation, altered states of consciousness, and increase of the brain's functional intelligence. Such an application of stimuli to a subject person and the reaction obtained is termed "multiple afferet sensory stimulation" or MASS.

These effects are produced through different combinations of visual and audio stimulus at different frequencies and in different rhythms. A total of four separate stimuli are available for energizing, one for each eye and for each ear, and such energizing may take many varied forms. The visual stimulus, if considering only one single color entity, such as an incondescent lamp, may have its brightness continually increased or decreased, may take the form of pulsed brief flashes of light which in turn can vary in brightness, or patterns over time or brillance can be formed with the pulses of light. For example, the pulses could be evenly spaced and of the same time width, and be increasing or decreasing in brightness, or the pulse repetition rate may be varied with or without the time period that the light is on or off fixed or varied. Further, the visual stimulus for each eye need not be the same.

The mode of operation of the audio stimulus can have many of the characteristics of the visual stimulus, such as pulsed tone, although, and perhaps preferably, music or pink noise may be substituted for a tone or combination of tones. The volume of the audio sounds can be increasing or decreasing, can consist of chopped sounds which again may be increasing or decreasing in intensity, and the duty cycle may be changed, i.e., the portion of the time that a sound is present compared to one complete cycle of sound present and not present.

Again, each sound stimulus for each ear need not be the same either.

Machines varying the visual and audio stimulus discussed above have been developed in the prior art.

It is reported that the human brain has basic frequencies at which it operates and which have been observed by recording equipment such as an electroencephalograph (EEG). These so called "brain waves" generally fall into four classifications in accordance with their frequency rate, namely Beta, Alpha, Theta, and Delta. Beta waves occur during a person's awake time and occupies a frequency spectrum of between approximately 12 and 30 Hz. (cycles per second). Generally, the higher the frequency the more intense mental activity. Alpha waves occur during relaxation and during that twilight state just before sleep. Alpha waves occupy the frequency spectrum of approximately 8 to 12 Hz. Theta waves represents the frequency spectrum between 4 and 8 Hz and generally reflect brain activity during sleep or deep meditation. Lastly, Delta waves occur during times of deepest sleep and are generally in the range of 1 to 4 Hz.

It has been determined by researchers, such as a Dr. George Corges, that a person's brain can be persuaded to operate in any of these four frequency spectrums by the application of visual and audio stimuli supplied in a desired frequency spectrum. The person's brain activity is "synchronized" with the frequency rate of the applied stimulus for certain defined stimulus.

By slaving the visual stimulus, such as repetitive blinking lights, with the audio stimulus, such as repetitive tones, a person will soon find their brain wave frequency, and thus mental activity, synchronizing to the applied visual or audio stimulus.

Obviously, various alternating modes of applied stimulus are possible by alternating between the left and right side eyes and ears in one or more of the sixteen possible combinations from no stimulus present on all four receptors (left and right eyes, left and right ears) to stimulus that all four receptors. In addition, the pattern of the stimulus can be varied as eluded to above.

Of course, some combinations of stimulus will result in less reaction of the person while other combinations of stimulus will result in a profound reaction.

Further, while it would be apparent that a scheme of application of structured visual and audio stimulus to a person would produce the best or desired reaction, yet it is possible to achieve desirable reactions by utilizing as the audio stimulus what is commonly termed "pink noise", which is a variation of "white noise". White noise is random electrical noise that exists in electronic circuits due to electron shot and thermal noise defined as having constant energy per unit band waves and independent of any central frequency of a band. The name is taken from the analogous definition of white light, which is the combination of lights of all colors in the light spectrum. Pink noise is white noise having the special characteristics that its intensity is inversely proportional to its frequency over a specified range. In pink noise, equal power is dissipated into a constant resistance in any octave band width in that range. Pink noise when heard, can have a very soothing effect, much like the sounds of ocean surf.

All of the stimulus, both visual and audio, with its variations, can be pre-programmed upon magnetic tape and then, through properly designed equipment, be presented to a person to achieve the desired mental and physical effects.

Accordingly, it would be useful to have a device adapted to take information pre-recorded on such a medium as magnetic tape, to decipher it through electronic circuits, and deliver the resultant electronic signals to generators of visual and audio stimulation surrounding a subject person.

SUMMARY OF THE INVENTION

The invention relates to a multiple afferent sensory stimulation device receiving on a prerecorded tape, a series of electronic signals which, after processing, control the placement of visual or sound stimulus before a subject person's eyes and ears.

The prerecorded tape, in the preferred embodiment, will have two channels upon each of which will be recorded the audio signals such as pink noise or music, which is to be heard by one of the subject persons's ears (left or right), while, upon the same channel is also recorded, the control signals regulating the visual stimulus for the same side eye, (left or right). Nominally, the visual control signal is of a higher frequency than the audio signal for one or more reasons, primarily however, in order that the subject person listening should not have the audio portion interrupted by a audible visual control signal. Secondly, simple filter means may be used to separate the audio signal from the visual stimulation signal. Nominally, two channels on the prerecorded tape are provided to the invention, one for the right side of the person's head (right eye and hear) and one for the left side of a person's head (left eye and ear). Obviously a four channel tape could be utilized, one channel for each receptor of the subject person.

The prerecorded tape is played back in the initial element of the invention, a playback device of some sort, such as a magnetic tape playback recorder, which output is divided into a left and right channel where each channel is to be separately processed by following electronic equipment. Since the processing circuitry which is the described invention and is the same for each channel, only one channel will be discussed.

The audio information and visual control electrical signals exit from the reproduction device upon an electrical line which bifurcates, one line going directly to an earphone which is the means which allows the person to hear the audio portion of the stimulus The signal also proceeds to a buffer amplifier where it is amplified for further processing. The signal at this point contains both the audio signal add the encoded visual stimulation control signal. Following the buffer amplifier, the two signals are separated by passing them through a high pass filter which rejects the lower audio portion and passes the high frequency control signal. Thereafter, only the high frequency visual stimulation control signal is processed.

Nominally, in the preferred embodiment, the audio range of signals which are recorded on the prerecorded tape and processed by the invention is in the range of 20 Hz to 20 kHz. and the high frequency visual stimulation control signals are in the range of 20 kHz. to 25 kHz. In the preferred embodiment, two visual stimulation control signals of 22.5 kHz. and 24 kHz. were selected. The higher frequency is the visual stimulus turn on signal and the lower frequency the turn off signal. Each channel will have both signals present.

To assure that a sufficiently large enough signal will be present for processing through logic circuits which are still ahead, it was found advantageous to follow the high pass filter with an automatic gain control circuit (AGC) which receives the high frequency signals and outputs the signals at a constant amplitude, regardless of their incoming amplitude. The signal is thereafter decoded by sending it to a pair of tone decoders, acting in parallel, one to search for signals having a specific frequency, say 24 kHz., and the other for the second specific frequency, nominally 22.5 kHz. Each of the tone decoders then will pass the information received at each of those frequencies, the output of the tone decoders comprising a pulsed signal of a logic level (+5 vdc) or ground (0 vdc). In order to insure that all of the visual stimulation control signals are processed by the invention, it has been found helpful to compare the output of one tone decoder with the second in a logic circuit to assure faithful reproduction of the control signals. The control signals are such that only one of the two frequencies are present at all times.

The output of the logic circuit is a series of logic level (0 or 1) pulses directed to the means by which visual stimulus is provided, namely a lamp driver, nominally a power amplifier, whose output is then used to pulse the visual stimulus, normally a lamp or perhaps a electronic shutter located between a source of light and a person's eyes.

It is an object of the subject invention to provide a device for processing the signals from a prerecorded tape to provide multiple afferent sensory stimulation of the auditory and visual senses.

It is another object to provide a multiple afferent sensory device which processes auditory and visual stimulus for separate audio and visual stimulus.

It is another object of the subject invention to provide a multiple afferent device which receives encoded signals from a prerecorded tape and separates the signals so that the auditory and visual stimulation devices may be separately controlled.

Other objects of the invention will in part be obvious and will in part appear hereinafter. The invention accordingly comprises the apparatus comprising the construction, combination of elements, and arrangement of parts which are exemplified in the following detailed disclosure, and the scope of the application which will be indicated.

BRIEF DESCRIPTION OF THE DRAWINGS

For further understanding of the nature and objects of the present invention, reference should be had to the following detailed description taken in connection with the accompanying drawings wherein.

In various views, like index numbers refer to like elements.

DETAILED DESCRIPTION OF THE PREFERRED EMBODIMENT

Figure 1:
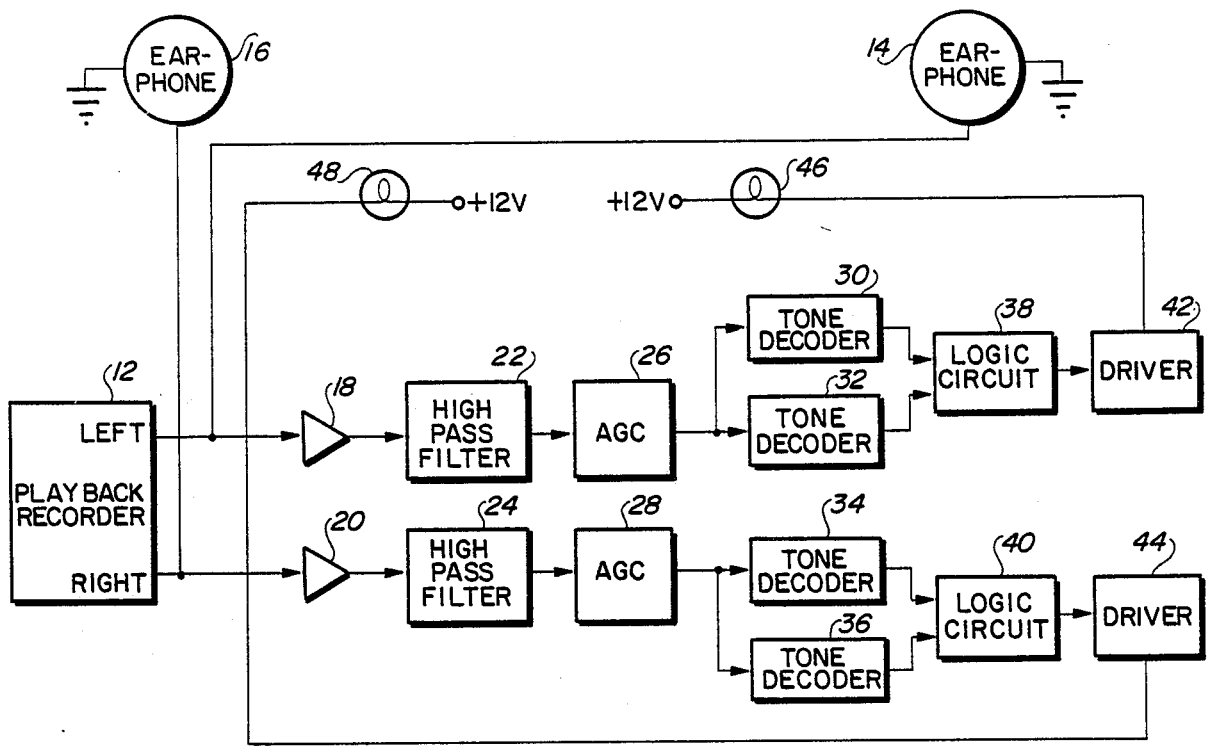
FIG. 1 is a block schematic diagram of the subject invention.

Referring firstly to FIG. 1, a block schematic diagram is shown of the invention which permits sensory stimulation of the visual and audio senses of a subject person, the stimulus in each of the patient's ears or eyes capable of being provided separately or together in all conceivable combinations. For example, one ear could be stimulated with sound without stimulating the other ear or visually stimulating either of the left or right eyes. The possible combination from no stimulus to any stimulus receptor (eyes or ears) to all four receptors receiving stimulus is 16 possible combinations.

Further, the combinations of stimulation is further increased because the light stimulation can be in combination of different brightnesses, or its brightness may be varied, either becoming more bright, or going less bright. Similarly, the audio stimulation can be at any volume, from very soft to very loud, or like the visual stimuli, may be increasing in volume or may be decreasing in volume. Further, both the audio and the visual stimulus can be pulsed in innumerable combinations. It is apparent that there is practically an unlimited number of combinations in which the four sensory organs may be stimulated.

Such sensory stimulation is accomplished by the circuit shown in FIG. 1. Proceeding from left to right, at the far left is the playback device such as a magnetic tape playback recorder or other machine which emits electrical signals on two channels, a left channel and a right channel. Playback device 12 outputs the two channel electrical signals from its input which for example may be a pre-programmed audio cassette tape. The audio tape has been pre-programmed with the desired sounds, such as music or pink noise, which may be either played very softly, very loudly, increasing or decreasing in volume, or may appear in spaced apart pulsations. Superimposed upon the music or other sounds on the tape are the visual control signals which regulate and operate the visual stimuli.

The electrical signals go immediately to the audio stimulation means, namely the appropriate left or right side of the headset worn by the subject person, the left earphone identified by the numeral 14 and the right earphone identified by the numeral 16. The other input to each earphone is grounded as shown in FIG. 1. The visual control signals are also present at the earphones, however, the earphone does not respond to electrical signals in their range (above 20 kHz.), or if the earphones do respond, the signals are above the subject person's hearing range. The left and right channels continue to buffer amplifiers 18 and 20 where the audio signals plus the visual stimulus control signals are amplified. At this point, discussion will continue along the left channel realizing of course that the very same discussion applies to the right channel since the circuit elements and components in each channel are identical. This does not, however, mean that the control signals on the left and the right channels are identical when the invention is being used, merely that the electronic hardware is.

Since it is not desirable, or even necessary, that the patient hear the control signals for the visual stimulus, the visual control signals are encoded on to the tape or other recorded mechanism which programs the visual stimulus is at a frequency outside the hearing range of a person, a frequency above 20 kiloherz (kHz.). Also, the visual control signals are recorded at a low volume.

To separate the encoded visual control signals from the audio portion, means such as high pass filters 22 and 24 are employed. These filters are designed to pass only frequencies greater than 20 kHz. In the preferred embodiment, two control frequencies utilized were 22.5 kHz. and 24 kHz. The higher of the two frequencies (24 kHz.) turns on the visual stimulus and the lower of the two frequencies (22.5 kHz.) turns off the visual stimulus. Only one frequency is present at a time. Following the high pass filters 22 and 24 is the electronic mechanism which assures that all the signals are of sufficient amplitude so that the later electronic processing equipment will receive all the information it is suppose to and therefore, automatic gain control (AGC) circuits 26 and 28 receive the electrical control signals from the high pass filters 22 and 24 respectively. Since in the preferred embodiment, two signals are used to turn on and turn off the visual stimulus, which in the preferred embodiment is a lamp situated immediately in front of the subject person's eyes, the electrical control signals are passed from the AGC circuits 26 and 28 to be decoded by a pair of tone decoders 30 and 32, and 34 and 36, left and right side. The tone decoders are essentially very narrow band pass filters which accept only a predetermined frequency signal and upon such receipt output a logic (1 or 0) level, for example, +5 vdc or 0 vdc, respectively.

In the preferred embodiment, the band width then of the turn-on tone decoder 30 (and 34) has a center frequency of 24 kHz. and a band pass of not greater than 1 kHz. Thus, all signals in the range of 23.5 kHz. to 24.5 kHz. will be received and acted upon by tone decoder 30. Similarly, tone decoder 32 (and tone decoder 36) is set to a center frequency of 22.5 kHz. with a band width of not greater than 1 kHz. Accordingly, signals in the range of 22.0 kHz. to 23.0 kHz. are acted upon by tone decoder 32 (and tone decoder 36). The control signals are preferably in the form of sine waves at the appropriate frequency.

Figure 2:
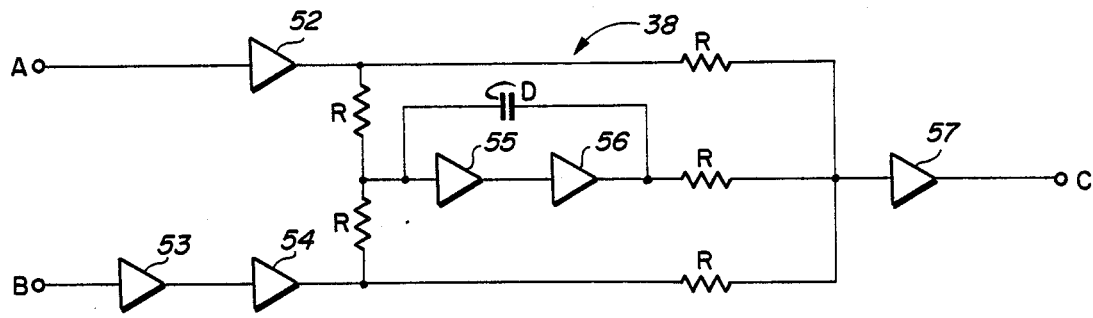
FIG. 2 is a block schematic diagram of the logic circuit of the invention.

Continuing with the block schematic diagram of FIG. 1, the signals process from the tone decoders 30 and 32 to logic circuit 38 (40 on the right channel) which receives both outputs for comparison to assure that in the event that there is some uncertainty in the decoder output signal, that by the comparison of the outputs of the tone decoders, the reliability of an output from the logic circuit is greater than the uncertainty of either one of the outputs of the tone decoder being correct. The tone decoders have been known to drop a signal, i.e., the output going to "0" for a short period of time when it should have remained a "1". Put in another way, logic circuit 38 assures that in the event one tone decoder errs, the other tone decoder assures that the logic circuit outputs the proper control signal. This assumes that both tone decoders do not err simultaneously. Logic circuit 38 is shown in FIG. 2 and discussed in connection with that Figure. From logic circuit 38, the visual stimulus control signal is directed to the means which provides the visual stimulus, namely lamp driver 42 (44 for the right channel) which is an amplifier that supplies current, and lamp 46 (48 on the right channel), which is energized by the electrical current. The other electrical connection to lamp 46 is the source of electrical energy, namely +12 volts dc.

Since, as mentioned above, the visual stimuli presented can be either a very soft, dim light, or a very bright light, or a light increasing in brightness or a light decreasing in brightness, together with the light on or off with respect to real time, i.e., a series of light pulses over time in a coded group of light pulses, or as a continuous light, the visual stimulation obtained is an average of the actual number of pulses present to energize the light. Since the patient's eye will not respond to frequencies greater than 60 cycles per second or so, a series of closely spaced pulses having a repetition greater than 60 Hz, for example, would appear to the subject person as a light constantly on. Similarly, if the on pulses are initially widely separated and then become closer spaced and are at a repetition rate greater than 60 Hz, the light will appear to a subject person as increasing in brightness. Certainly the inverse is true, from pulses which are closely spaced to pulses which are spaced apart with respect to time will cause the light to appear to reduce its intensity over the period of time. If the light utilized is an incandescent bulb, it will take some period of time before it emits light from the time that the electrical pulse is received as the filament must heat up to the point of emitting the light. Plus, in the case of incandescent lights, the filament tends to stay hot and emit light for a period after the pulse has passed. Thus, the incandescent bulbs may be made to have its light energy waning, or increasing, or pulsing, when all it is, is the spacing of strings of electrical pulses.

Obviously then, a pulse width modulation can be used as the procedure for producing the visual stimuli control pulses.

In the preferred embodiment, the elements described in FIG. 1 comprise the following commercially available electronic circuits: amplifier 18 is a National Semiconductor LM741; the high pass filter 22 is a Gould Electronics programmable high pass filter S3529; the AGC circuit 26 is a circuit adapted from *Applications of Operational Amplifiers*, McGraw Hill, by Jerald g. Graeme, p. 218; and tone decoders 30 and 32 were National Semiconductors LM567 general purpose tone decoders designed to provide a saturated transistor switch to ground when an input signal is present within the pass band. The elements utilized in logic circuit 38, as will be further explained in connection with FIG. 2, were Motorola MC14069UB low power complementary MOS inverters, and lamp driver 42 was Siliconix VN2222L.

Referring now to FIG. 2, a detailed block schematic diagram of logic circuit 38 (40 in the right channel) is detailed. The integrated circuits represented by triangle shapes are all logic inverters adapted to receive a signal and invert it to its opposite logic level. For example, "0" becomes a "1" and "1" becomes a "0". In the preferred embodiment, 0 volts dc was utilized as the "0" logic level and +5 volts dc is the logic level "1". The inputs, letters "A" and "B" are representative of the two outputs from the two tone decoders 30 and 32, and the output "C", the single output of logic circuit 38 shown in FIG. 1.

Commencing firstly at input "A", whenever a "0" appears at the input, a "1" appears on the output of inverter 52. On input "B" for a 0 at the input to the first inverter 53 a 1 would appear at inverter 53's output, which in turn is the input for inverter 54 causing a "0" to appear on the output of inverter 54. Both of these logic levels, the outputs of inverters 52 and 54, are conducted to the input of inverter 55, the output of which is conducted to the input of series inverter 56. Thus, for a "0" input to inverter 55, a 1 appears on its output, and thus on the input of inverter 56 causing a 0 to appear on the output of inverter 56. The logic level 0 at the output of inverter 56 is then conducted to the joinder point between the outputs of inverters 52 and 54 and, in this case, all being 0's will place a 0 on the input to the final inverter 57 resulting in a "1" logic output from this final inverter.

Thus, it is apparent that from the beginning through the end of the logic circuit 38, a "1" on the input of A resulted in a "1" on the output C. In the event that the input "B" were changed to a 1 resulting in both 1's on inputs A and B which should not be the case since only one frequency (22.5 or 24 kHz.) is present at a time and the outputs of the tone decoders should not be the same, two "1's " would be an error), a 0 would appear on the output of inverter 52 and a 1 on the output of inverter 54. These two outputs are summed for the input of inverter 55 and would result in a 1 on the input of inverter 55 and a 1 on the output of inverter 56 except for the presence of feedback capacitor "D" which tends to average the input of inverter 55. If the 1 on inverter 53 input were short lived, the input to inverter 55 would remain 0 and the output "C" not be changed.

For the opposite case, i.e., A is 0 and B is 1, the output of C is 0. This represents the situation of when the off frequency (22.5 kHz.) is present.

Thus it is apparent that the output C will be 1 for inputs of A being 1 and B being 0; output C being 0 for A being 0 and B being 1. The output C does not change due to spurious outputs from the tone decoders.

In the logic circuit 38 shown in FIG. 2, all the resistor "R" values are typically in the order of 10 k ohms. The sole capacitor "D" is 0.047 uF. The inverters were all part of a single integrated circuit, namely Motorola MC14069UB, a low power complimentary MOS hex inverter.

Figure 3:
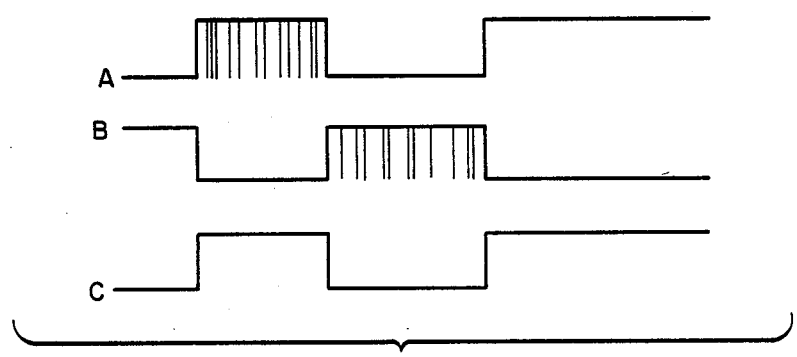
FIG. 3 is a representation of the input and output signals of the logic circuit.

The purpose of the logic circuit shown in FIG. 2 is more fully explained when the signals shown in FIG. 3 are discussed. Because there is a likelihood that there may be uncertainty in the output signals from the tone decoder, the circuit of FIG. 2 increases the certainty of an appropriate output.

Referring now to FIG. 3, inputs A and B together with the resultant output C (refer to FIG. 2) are shown in what might be an output of tone decoders 30 and 32. The output A (output of tone decoder 30) is 0 when starting and then rises to a logic level 1 for a period of time and then falls back to 0 for a second period of time and then rises to a 1 again. Input B (output of tone decoder 32) is the inverse of A and commences at a level 1 falling to a level 0 at the time that the input A rises to a level 1. This continues for the same initial time period as above discussed, input B rising to a 1 at the same time that input A falls to 0. This then continues over the second period of time with 10 input B then falling to 0 from 1 and input A rising from 0 to 1. As is evident in the illustration of inputs A and B, A and B both have uncertainties in the signals when the signals are a logic 1. Here, for example, input A, during the period of time that it is primarily in logic 1, has very short instances of time when it falls to 0 as illustrated by the up and downward going lines within its pulse width. The same situation applies to input B. To assure that the output C does have greater certainty than the inputs A and B, the circuit illustrated in FIG. 2 is utilized and as can be seen by the representative output C of FIG. 3, the resulting output wave form is a solid logic pulse over the period of time it is suppose to be solid and a clean output pulse C is generated.

Figure 4:
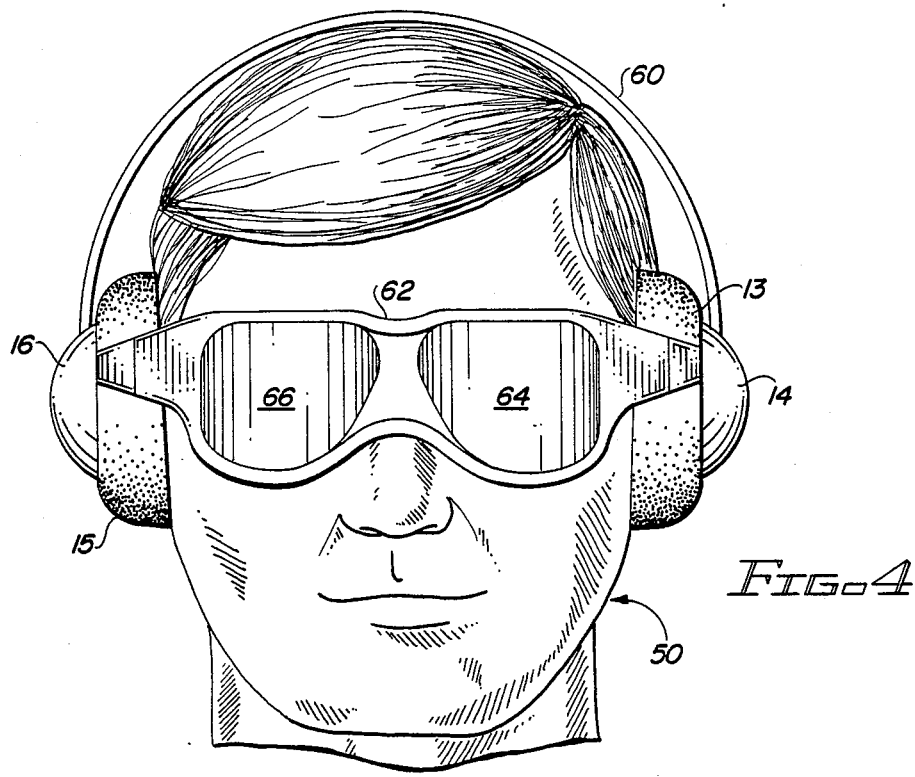
FIG. 4 is a front view of a subject wearing the earphones and goggles receiving the audio and visual stimuli.

FIG. 4 is a perspective view of a patient utilizing the apparatus of the invention showing firstly the left and right earphones, 14 and 16 respectively, of headset 60 mounted upon the head of the user 50. The headset is preferably spring loaded in the band connected to the two earphones so as to hold each earphone to the ear, each earphone utilizing a elastic cushion 13 and 15 situated between the earphone and the ear so as to provide comfort to the user and to keep out extraneous sounds from interfering with the programmed audio sounds heard by user 50. Situated proximate each of the user's eyes are a pair of goggles 62 which contain individual opaque lens, left opaque lens 64 and right opaque lens 66, each separated from the other and light protected. Immediately behind each of lens 64 and 66 are lamps 46 and 48 (FIG. 5), being the left and right lamp respectively. Thus, the subject person 50 shown in the diagram of FIG. 4 has four inputs of audio or visual stimulus, each separated from the other and each capable of being separately energized with an appropriate sound or light stimulus.

Figure 5:
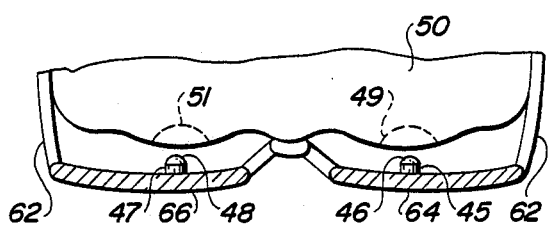
FIGS. 5-8 are top partial views of a subject wearing the goggles with the different types of visual stimulus situated immediately before the subject's eyes or with an electronic shutter interposed the eyes and the stimulus.

FIG. 5 is a top cutaway view of the opaque lens showing the lamp interposed between the lens and the subject person's eyes. In FIG. 5, lens 64 and 66 are shown in goggles 62, goggles 62 so arranged with surrounding padding so as to prevent light passing from the outside into the interior portion where the subject person's eyes 49 and 51 are shown. Lamps 46 and 48 are shown mounted generally in front of the eyes upon a mount 45 and 47 which are attached to the respective left and right lens.

Figure 6:
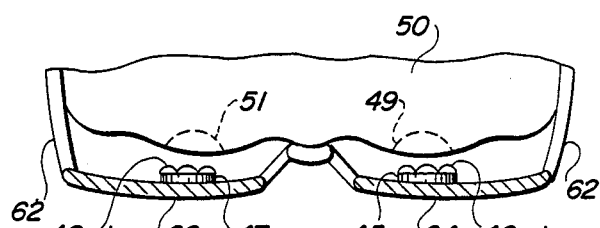

An alternate embodiment of the visual stimulus is shown in FIG. 6 where, instead of a single lamp in front of each eye, three lamps have been placed before each eye, each lamp capable of emitting a different color, perhaps by coating the glass envelope of the lamp. The lamps are enumerated 46a, 46b, and 46c, for the left lamp and 48a, 48b, and 48c, for the right lamp. It is suggested that the primary colors of red, green, and blue be utilized as the three lights emitted from the lamps. The lamps are mounted to the left and right opaque lenses by means of lamp mounts 45a and 47a which attach to both the lamps and to the opaque lenses. Shown in FIG. 6, like FIG. 5, are the eyes 49 and 51 of the subject person, and the goggles. Like FIG. 5, FIG. 6 is a cutaway top view showing the user, the lamps, and the lenses.

It is realized of course that if a system such as shown in FIG. 6 is utilized, the basic circuit shown in FIG. 1 would have to be modified in ways which are obvious to one skilled in the art. Simply, each left and right side channel of the circuit shown in FIG. 1 could be trebled in part so that each of the primary color lamps passes through its own circuit from tone decoders 30 and 32 through lamp driver 42. In such case, each of adjustable tone decoders would necessarily be set to decode one of the six required specific frequencies, each output of reproducing device 12 being such that the six total signal frequencies are present along with the audio portion.

Figure 7:
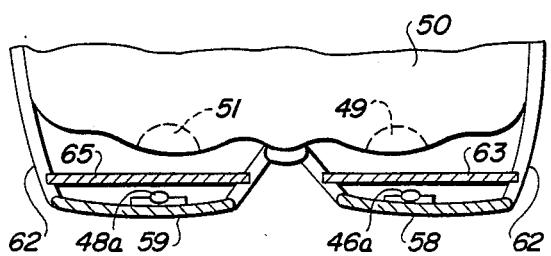

Next, a third embodiment of the invention is shown in FIG. 7 where the lamps have been placed outside the normally opaque lenses and the opaque lenses have been replaced with electrically operable light LCD filters or shutters. For example, referring to FIG. 7, the electrically operable light filters or shutters are shown as numerals 63 and 65 situated between the eyes 49 and 51 of subject person 50 respectively and the source of light, namely lamps 46a and 48a. In this case, the electrical signals from the lamp driver 42 and 44 respectively of FIG. 1 drives and varies the light filtering of the LCD filters or operation of the shutters 63 and 65 and lamps 46a and 48a are continually emitting light, the light seen by the person then being controlled by the filters or shutters. Providing a support for the lamps 46a and 48a are covers 58 and 59, preferably opaque covers so that any third party watching the user will not necessarily be distracted by lights in front of the user's eyes.

Further, in FIG. 7, it would be possible to remove the lamps 46a and 48a, replace the covers 58 and 59 with light diffusers such as sheet mylar, and then use the sun as a source of light. In such case, the shutters 63 and 65 control the passage of light into the person's eyes.

Figure 8:
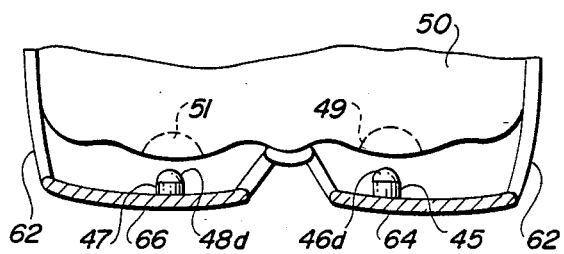

One last embodiment is shown in FIG. 8 wherein the lamps 46 and 48 of FIG. 5 have been replaced by Bonar Kard-0-Lite electro eluminesent devices which are capacitors but act as light sources when pulsed, namely numerals 46d and 48d.

It is patently obvious that the medium used to store the programmed audio and visual stimulus control signals may take on prerecorded form, such as magnetic tape, punched tape, or laser encoded disk. In such case, the reproducing device 12 need only be the appropriate playback device.

While a preferred embodiment and three alternate embodiments have been shown and described, it will be understood that there is no intent to limit the invention by such disclosure, but rather it is intended to cover all modifications and alternate constructions falling within the spirit and the scope of the invention as defined in the appended claims.

I claim:

1. A multiple afferent sensory stimulation device providing audio and visual sensory stimulation to a patient comprising:
    a playback device adapted to receive a pre-recorded program and to emit audio stimulation signals and a plurality of visual stimulation control signals;
    means operably connected to said playback device to separate the visual stimulation control signals from the audio stimulation control signals, said means including a high pass filter to block the audio stimulation signals while passing the visual stimulation control signals;
    means operably connected to said playback device to provide audio stimulation to at least one of the patient's ears;
    a pair of tone decoders operably connected to said means separating the visual stimulation control signals from the audio stimulation signals, one of said tone decoders adapted to emit a signal output upon receipt of a visual stimulation control signal of a first frequency, and a second of said tone decoders adapted to emit a signal output upon receipt of a visual stimulation control signal of a second frequency;
    a logic circuit connected to said pair of tone decoders adapted to receive signal outputs from said first and second tone decoders, said logic circuit adapted to ignore false signals from either said first or second tone decoders; and
    means operably connected to said tone decoders to receive the decoded visual stimulation control signals for displaying visual stimulation to at least one of the patient's eyes whereby audio and visual stimulation is provided a patient in accordance with the pre-recorded program to induce sensory reactions into the patient.

2. The multiple afferent sensory stimulation device as defined in claim 1 wherein said means operably connected to said pair of tone decoders to receive the decoded visual stimulation control signals defines a lamp driver and a lamp adapted to be positioned proximate one of the patient's eye.

3. The multiple afferent sensory stimulation device as defined in claim 2 wherein said means operably connected to said playback device to separate the visual stimulation control signals from the audio stimulation signals includes an amplifier whose output is connected to said high pass filter, said amplifier's input connected to said playback device.

4. The multiple afferent sensory stimulation device as defined in claim 3 further including an automatic gain control circuit operably attached to said high pass filter and to said tone decoders, said automatic gain control circuit receiving the visual stimulation control signals from said high pass filter, controlling the visual stimulation control signals to a fixed amplitude, and transmitting the visual stimulation control signals to said tone decoders.

5. The multiple afferent, sensory stimulation device as defined in claim 4 wherein said means operably connected to said playback device to provide audio stimulation to at least one of the patient's ears defines an earphone.

6. The multiple afferent sensory stimulation device as defined in claim 5 wherein said playback device comprises a magnetic tape recorder.

7. The multiple afferent sensory stimulation device as defined in claim 6 wherein said means operably connected to said tone decoders to receive the decoded visual stimulation control signals and display visual stimulation includes a light shutter connected to said lamp driver, said light shutter is adapted to be situated between a source of light and one of the associated patient's eyes.

8. The multiple afferent sensory stimulation device as defined in claim 5 further including:
   second means operably connected to said playback device to separate the visual stimulation control signals from the audio stimulation signals, said second means including a high pass filter to block the audio stimulation signals while passing the visual stimulation control signals:
   second means operably connected to said playback device to provide audio stimulation to the second of the patient's ears;
   a second pair of tone decoders operably connected to said means separating the visual stimulation control signals from the audio stimulation signals, one of said second pair of tone decoders adapted to emit a signal output upon receipt of a visual stimulation control signal of a first frequency, and a second of said tone decoders adapted to emit a signal output upon receipt of a visual stimulation control signal of a second frequency;
   a second logic circuit connected to said second pair of pair of tone decoders adapted to receive signal outputs from said first and second of said second pair of tone decoders, said logic circuit adapted to ignore false signals from either said first or second tone decoders; and
   a second means operably connected to said tone decoders to receive the decoded visual stimulation control signals for displaying visual stimulation to the second of the patient's eyes whereby audio and visual stimulation is adapted to provide to all of a patient's visual and audio receptors in accordance with the pre-recorded program and to induce sensory reactions into the patient.

9. The multiple afferent sensory stimulation device as defined in claim 5 wherein said playback device comprises a reproducing device adapted to receive said pre-recorded program on a laser encoded disk.

10. The multiple afferent sensory stimulation device as defined in claim 5 wherein said means operably connected to said tone decoders to receive the decoded visual stimulation control signals and display visual stimulation further includes a pair of goggles, said goggles having a pair of opaque lenses, one lens adapted to be positioned proximate each of the patient's eyes, said lenses adapted to secure each of said lamps between said lens and the associated patient's eye.

11. The multiple afferent sensory stimulation device as defined in claim 1 wherein said means operably connected to said tone decoders to receive the decoded visual stimulation control signals and display visual stimulation includes an electro eluminescent device is adapted to be situated proximate the associated patient's eye.

* * * * *